(12) United States Patent
Moon et al.

(10) Patent No.: US 6,241,975 B1
(45) Date of Patent: Jun. 5, 2001

(54) METHOD FOR PREPARATION OF PLANT EXTRACT POWDER

(75) Inventors: Hyun Soo Moon, Seoul; Byung Ryeul Lee, Yongin; Key Hyun Lee, Seoul, all of (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/478,356

(22) Filed: Jan. 6, 2000

(30) Foreign Application Priority Data

Jul. 24, 1999 (KR) .................................................. 99-30186
Oct. 6, 1999 (KR) .................................................. 99-43040

(51) Int. Cl.[7] .............................. A61K 7/26; A61K 9/14; A61K 9/16; A01N 65/00
(52) U.S. Cl. ........................... 424/58; 424/489; 424/490; 424/195.1
(58) Field of Search ..................... 424/401, 490, 424/489, 70.17, 70.11, 195.1, 435, 408, 498

(56) References Cited

U.S. PATENT DOCUMENTS

| | | | |
|---|---|---|---|
| 4,071,614 | * 1/1978 | Grimm, III | 424/49 |
| 4,689,216 | 8/1987 | Greene | 424/58 |
| 4,919,933 | * 4/1990 | Park et al. | 424/196.1 |
| 5,239,079 | * 8/1993 | Souda et al. | 546/271 |

FOREIGN PATENT DOCUMENTS

| | | |
|---|---|---|
| 58-134013 | 8/1983 | (JP) . |
| 62-138420 | 6/1987 | (JP) . |
| 9-110663 | 4/1997 | (JP) . |

\* cited by examiner

*Primary Examiner*—Jon P. Weber
*Assistant Examiner*—Patricia Patten
(74) *Attorney, Agent, or Firm*—Foley & Lardner

(57) ABSTRACT

The present invention relates to a method for preparation of plant extract powder and oral compositions containing plant extract powder prepared by the same. More particularly, the present invention could provide a method for preparation of plant extract powder comprising the steps of (a) loading a plant extract having activities of prevention of and treatment for periodontal diseases or tooth decay into a porous powder carrier; (b) coating said carrier's surface with a water-insoluble coating agent and oral compositions containing plant extract powder prepared by the above described method which have an excellent periodontal diseases preventing effect and tooth decay preventing effect.

6 Claims, No Drawings

METHOD FOR PREPARATION OF PLANT EXTRACT POWDER

BACKGROUND OF THE INVENTION

1. Field of the Invention

The present invention relates to a method for preparation of plant extract powder and oral compositions containing plant extract powder prepared by the same.

2. Description of the Related Arts

To keep teeth healthy and normal is directly related to the maintenance of body's health as well as that of mouth. After having been grown to a certain age, teeth are not be reconstructed nor regenerated and they are exposed to various agents or unclean oral environments which could cause serious dental diseases.

It is generally known that tooth decay and periodontal diseases, which occupy most of oral diseases, are caused by plaque which is generated by oral microbe colony at the teeth's surface. When saliva forms a sticky thin film covering the teeth's surface, the microbes can form colony there. That is to say, tooth decay is caused by corrosion of enamel which occurs when Hydroxyapatite, a main ingredient of teeth, is dissolved by organic acid produced when anaerobic bacteria in plaque metabolize the saccharides. And periodontal diseases are caused by the accompanying accumulation of plaque which overwhelms the host's protection ability. Therefore, to alleviate the periodontal diseases, the activity of causative bacteria of periodontal diseases has to be suppressed and hematocele of gum having inflammation has to be improved and the gum inflammation has to be alleviated.

To prevent tooth decay and periodontal diseases, it has been used fluoride compounds to prevent the corrosion of enamel and antibiotics such as penicillin, erythromycin, tetracycline or antibacterial agents such as chlorhexidine to die out tooth decaying bacteria. But the excess use of fluorine causes the hardening of cartilage and stomachache and the use of bactericides or antibacterial agents cause various side-effects in the mouth.

Therefore, instead of using artificial antibiotics and bactericides, it has been proposed to use medicinal plant extracts which have an effect on causative bacteria of tooth decay and periodontal diseases. Representative examples include Sanguinaria extract(U.S. Pat. No. 4,689,216), Myrrh, Rhatany, Sage, Chamomile and Echinaecia extract (S. de Rysky; Journal of Clinical Dentistry Vol. I. Supplement A. A22–24, 1988), Sage and Rosemary extract (Japanese Patent Publication Sho 58-134,013), or Hop extract(Japanese Patent Publication Sho 62-138,420). But, these various plant extracts are not stable in the formulation products so that the phase separation of composition is easily occurred.

Therefore, several attempts have been made to stabilize the active principles in the oral compositions. For example, the use of gel capsule to stabilize the oil-soluble ingredient is disclosed in the Japanese Patent Publication Hei 9-110663 as a method for stabilizing the effective ingredients in the oral composition. This gel capsule was prepared through dipping or absorbing the oil-soluble ingredient in inorganic or organic powder carrier and coating it with water-soluble high molecular substance's gel film. But there still exists the problem of instability of composition because the water-soluble coating could be melted when it is injected into the liquid phase oral compositions such as toothpaste during production process or storage.

SUMMARY OF THE INVENTION

The present invention provides a method for preparation of plant extract powder, which comprises the steps of
(a) loading a plant extract having activities of prevention of and treatment for periodontal diseases or tooth decay into a porous powder carrier;
(b) coating said carrier's surface with a water-insoluble coating agent.

The present invention further provides oral compositions containing plant extract powder prepared by the above described method which have an excellent periodontal diseases preventing effect and tooth decay preventing effect.

The present invention will be described in detail below.

DETAILED DESCRIPTION OF THE INVENTION

According to the present invention, the method for preparation of the plant extract powder is characterized in that which comprises the steps of (a) loading a plant extract having activities of prevention of and treatment for periodontal diseases or tooth decay into a porous powder carrier; (b) coating said carrier's surface with a water-insoluble coating agent.

Also, the oral composition of the present invention is characterized in that which contains the plant extract powder prepared by this invention in an amount of 0.05~5.0% by weight.

The method for preparation of the plant extract powder will be described in detail hereinafter.

The step (a) is to load a plant extract having activities of prevention of and treatment for periodontal diseases or tooth decay into a porous powder carrier. Plants which are used in the present invention in the form of extract to treat oral diseases may be selected from one or more of pine, licorice, cassia seed, cinnamon, nothosmyrnium root, sophora, lonicera flower, platycodon, green tea, dayflower, Korean angelica root, liriope rhizome, moutan, Arabian myrrh, seseleos radix, *Angelicae Dahuricae Radix, Lagerstroemia indica,* morus bark, ginger, sanguinaria, asarum, cimicifuga, Chinese galls, Grapefruit seed, lycium root, cnidium, *Alpinia katsumadai Hayata,* gardenia, *Lythrum salicaria L.,* dandelion, propolis, flavonoid, nepta herb, *Reynoutria japonica Houtt.,* scutellaria, machilia, black adzuki bean, camomile, ratanhia or Sage oil.

The extraction can be carried out by the general extraction methods such as alcohol digestion, steam distillation, supercritical fluid extraction method by adding cosolvent and the like.

In case of Pine extract, it is used as a form of mixture solution with salt, of which effectiveness of prevention and treatment for periodontal diseases such as gingivitis, alveolar pyorrhea due to astriction to the gum is known, and the mixing ratio of pine extract and salt is 1:0.1~10 by weight.

While there exist various problems in the use of chemical components, which are generally used in oral composition as effective ingredients at present, because diffused chemical components in the mouth could eliminate or dilute the product of bacteria such as enzymes, toxins and antigens as well as bring the direct destruction of component materials of dental plaque so that there coexist various problems such as manufacturing concentration, dose and etc., we could expect the antibiotic, anti-inflammatory and analgesic action of above described plant extracts because they contain essential oils, triterpens, flavonoids, iridoids, alkaloids and etc.

The carrier of the present invention for loading the plant extract may be porous materials("carrier 1") having particle size of 5~600 μm, preferably 100~400 μm; or porous materials("carrier 2") having a primary particle size of 1~100 nm are used.

For the carrier 1, any kind of powder, which has appropriate suction force, chemical stability and physical stability, could be commonly used in the skilled of the art. The examples of powder of the present invention are calcium monohydrogen phosphate, calcium pyrophosphate, calcium carbonate, silicon dioxide, aluminum hydroxide, and insoluble sodium metaphosphate. Also, inorganic abrasives such as aluminum silicate, zirconium silicate, zeolite, aluminum magnesium silicate, diatomite or zirconium oxide and the like can be used as well. Also, the abrasives of high molecular substances, which have been employed in tooth pastes, are useful as carrier for plant extracts because they never release the calcium ion so that fluoride compound, which is the component of an efficacy of a medicine, never lose activation by being disused. The example of high molecular substances as carrier may include, but not limited to, polyethylene, polyvinylchloride, polyester, polystyrene, polypropylene, polyamide, polycarbonate, phenol resins, urea resins, polymethylmetacrylate resins or melamine resins. While, among abrasives of high molecular substances, polyethylene and polyvinylchloride are more preferable.

For the carrier 2, colloidal fumed silica having particle size of submicron could be used because it could more easily disperse in the liquid formulation like oral purifier than having larger particle size does and it has more surface area than having same mass with larger particle size has so that it could well adhere to the oral tissue due to increasing contact area.

When the plant extract is loaded into a carrier, it's preferable to load plant extract into a carrier in the ratio of 1:1~10 by weight.

The step (b) is to coat said carrier's surface with a water-insoluble coating agent.

Carrier loaded into plant extract could be applicable in itself, but there exists a few problems. That is to say, oral compositions are mostly water solution system so it is meaningless to load plant extract into a carrier because the water soluble materials could be released from carrier. Therefore, the surface of carrier being loaded into plant extract should be coated with the water-insoluble materials.

But the coating agent to coat the surface of carrier has to be easily disintegrated in the mouth so that the extract contained in the oral composition could be easily released when being applied into the mouth.

Therefore, the coating agent of the present invention is selected from one or more of polyethylene glycol, methyl cellulose, hydroxypropylcellulose, hydroxypropylmethylcellulose, ethylcellulose, hydroxyethylcellulose, polyvinylalcohol, vinylpyrrolidon, vinylacetate copolymer, polyvinylacetaldimethylaminoacetate, polymethylmetaacrylate, bees wax, paraffin wax, carnauba wax and petroleum wax which are water-insoluble and have solid structure that could be disintegrated by mechanical stimulus.

The above-described coating agent of the present invention could easily release the extract in the oral composition such as toothpaste by mechanical strength like brushing the teeth, but it's releasing effect in liquid oral purifier in which the mechanical strength would be relatively lower than that of toothpaste so we had continuously investigated to find the coating agent applicable for both liquid oral purifier and toothpaste materials.

As a result, we have found that it could be achieved the above object by coating the above carrier with material which is water-insoluble and decomposable by one or more enzymes existing in saliva.

That is to say, because there exist lipases, proteases, glucosidases in saliva and in the special cases there exist parotid amylase, hyaluronidase, β-glucuronidase, chondroitin sulfatase, amino acid decarboxylases, catalase, peroxidase, collagenase, lysozyme and etc. in saliva, so the carriers of which surface are coated with polyhydroxyalkanoic acid, glycolipids, glycerides or phospholipids could be decomposed by those enzymes in saliva.

The coating can be carried out by the coating methods which could be suitably chosen from the surface coating methods known in the art. For example, by mixing coating agent and carrier and then heating it to coat the surface of carrier(the coating temperature varies depending on the melting temperature of coating agent. In case of carnauba wax, the coating is executed at a temperature of 85~95 ° C.). The mixing ratio of carrier and coating agent is 1:0.5~20 by weight, and 1: 1~5 by weight is more preferable. Also, when glyceride, phospholipid, glycolipid, which could be disintegrated by heating temperature, are used, coating is executed by dissolving coating agent in suitable solvent and then absorbing it into carrier and volatilizing the solvent(Alcohol is used as solvent in case of one of phospholipids of phosphatidylcholine).

Plant extract powder prepared by the above method is contained in the oral compositions, and the content of which is 0.05~5% by weight of total oral composition, 0.1~3% by weight of total oral composition is more preferable.

Although the oral compositions of the present invention are not specially limited in it's formulation, specifically they could have a formulation such as toothpaste, oral cleaner, oral purifier.

Also, other conventional components of oral compositions, excluding plant extract powder, could be suitably chosen and mixed according to the formulation or desired effects by those of skilled in the art.

For example, toothpaste could contain abrasives, humectant, foaming agent, coupling agent, sweetening agent, pH control agent, antiseptic, ingredient having efficacy of a medicine, flavoring agent, whitening agent, pigment, solvent and etc. The examples of abrasives are calcium carbonate, settling silica, aluminum hydroxide, calcium monohydrogen phosphate, insoluble sodium metaphosphate, and these abrasives may be used in single or combinations thereof in an amount of 1~60% by weight, and 10~50% by weight is more preferable.

The examples of humectants are glycerin, sorbitol solution, polyethyleneglycol, propyleneglycol and these humectants may be used in single or combinations thereof in an amount of 10~60% by weight, and 20~50% by weight is more preferable.

The examples of forming agents are anionic and nonionic surfactant such as sodium lauryl sulfate, sodium lauryl sarcosinate, sucrose fatty acid ester, polyoxyethylene hardening castor oil, polyoxyethylenepolyoxypropylene copolymer and they may be used in single or combinations thereof in an amount of 0.5~5% by weight, and 0.5~3% by weight is more preferable.

The examples of coupling agent are sodium carboxymethyl celluose, hydroxymethyl celluose, carrageenan, xanthan gum, sodium alginate and they may be used in single or combinations thereof in an amount of 0.1~5% by weight, and 0.1~2% by weight is more preferable.

The examples of sweetening agent are sodium saccharin, aspartame, stevioside, xylitol, glycyrrhizic acid and they may be used in single or combinations thereof in an amount of 0.05~5% by weight.

The examples of pH control agents are sodium phosphate, disodium phosphate, trisodium phosphate, sodium pyrophosphate, citric acid, sodium citrate, tartaric acid and the examples of antiseptic are paraoxybenzoate methyl, paraoxybenzoate propyl, sodium benzoate and they may be used in single or combinations thereof.

The examples of ingredient having efficacy of a medicine are sodium fluoride, sodium mono fluorophosphate, tartaric fluoride, chloro hexydyn, allantoin chlorohydroxyaluminate, amino caproic acid, tranexamic acid, triclosan, cetyl pyridium chloride, zinc chloride, hydrochloric acid pyridoxin, acetate tocopherol and they may be used in single or combinations thereof.

Flavoring agents used in the present invention may be an appropriate mixture of peppermint oil, menthol and anethole and whitening agent used in the present invention is titanium oxide and pigment used in the present invention is edible pigment and the solvent used in the present invention is purified water and ethanol.

The present invention will be described by way of various experimental examples and examples to explain the method for preparation of plant extract powder and the composition and effect of action of oral compositions containing plant extract powder prepared by the same in detail. But, it should not be interpreted that the present invention to be limited to these examples.

EXAMPLE 1

To the mixture of pine needle extract(20 g) with refined salt, purified water(200 g) was added and dissolved the mixture solution not to remain salt particles. Precipitated silica(200 g) having particle size 400 μm was added to the mixture solution with stirring to load. And then thin slice of carnauba wax(200 g) and loading silica particles were mixed together and heated at a temperature of 85~95° C. The resulting coated pine salts(398 g) were obtained.

EXAMPLE 2

To the mixture of pine needle(20 g) with refined salt, purified water(200 g) was added and dissolved the mixture solution not to remain salt particles. Fumed silica(200 g) having a primary particle size 40 nm was stirred into the mixture solution to load. And then phosphatidylcholine(200 g; having acid value of about 20 and having wax form), one of phospholipids was dissolved into cold ethanol(2,400 g). Prepared phosphatidylcholine-ethanol solution and loading silica particles were mixed together and distilled under reduced pressure with stirring. After ethanol being volatilized, the resulting coated pine salts(398 g) were obtained.

Comparative Example 1

By heating a mixture of resin(10 g) with salt(20 g) at a temperature of 700~800° C. to obtain crystal salt, it was pulverized and then resin(20 g) was added thereto and heated strongly at a temperature of 1,000~1,500° C. After being quickly cooled down and pulverized, the resulting pine salt was obtained.

Experimental Example 1

We prepared the toothpaste from oral composition containing above prepared pine salt according to the general toothpaste preparation method with a formulation of Table 1 below.

TABLE 1

| INGREDIENT | Comp. Formulation 1 | Comp. Formulation 2 | Formulation 1 | Formulation 2 |
|---|---|---|---|---|
| Hydrated silicic acid | 15 | 15 | 15 | 15 |
| Sodium fluoride | 0.22 | 0.22 | 0.22 | 0.22 |
| Glycerin | 5 | 5 | 5 | 5 |
| Sorbitol solution | 35 | 35 | 35 | 35 |
| Carboxy methyl sodium celluose | 0.5 | 0.5 | 0.5 | 0.5 |
| Sodium lauryl sulfate | 2.0 | 2.0 | 2.0 | 2.0 |
| Methyl paraben | 0.15 | 0.15 | 0.15 | 0.15 |
| Flavoring agent | 1.0 | 1.0 | 1.0 | 1.0 |
| Pine needle extract | 1.0 | — | — | — |
| Refined salt | 1.0 | — | — | — |
| Pine salt(Ex. 1) | — | — | 1.0 | — |
| Pine salt(Ex. 2) | — | — | — | 1.0 |
| Pine salt (Comp. Ex. 1) | — | 1.0 | — | — |
| Titanium dioxide | 0.4 | 0.4 | 0.4 | 0.4 |
| Sodium saccharin | 0.2 | 0.2 | 0.2 | 0.2 |
| Purified water | To 100 | To 100 | To 100 | To 100 |

Testing bacilli strains were scratched onto individual agar plates containing the above toothpaste of formulation 1~2 and comparative formulation 1~2 in a various concentration. In case of bacillus of periodontal disease after being cultivated at 35° C., for 5 days under anaerobic conditions, their growth were observed. And in case of causative bacillus of tooth decay after being cultivated for 2 days under aerobic conditions, their growth were observed, and the minimum concentration of testing bacillus at which they were not grown were measured to identify the antibacterial action against bacillus of tooth decay and causative bacillus of periodontal disease. The results are shown in Table 2.

(1) Testing Bacillus

① Causative bacillus of Periodontal disease: *Actionbacillus actinomycetecomitans*(ATCC29522), *Fusobacterium nucleatum*(ATCC29586)

② Causative bacillus of tooth decay: *Streptococcus mutans*(NCTC10449), *Actinomyces viscosus*(ATCC15987)

(2) Culture Medium

Blood agar medium(blood agar base+blood which makes the final concentration as 5%), BHI agar

TABLE 2

(Minimum Inhibitory Concentration(MIC))

| Testing bacillus | Comp. Formulation 1 | Comp. Formulation 2 | Formulation 1 | Formulation 2 |
|---|---|---|---|---|
| *Actionbacillus actinomycetemcomitans* | 2(50) | 1(100) | 0.5(200) | 0.5(200) |
| *Fusobacterium nucleatum* | 2(50) | 1(100) | 0.5(200) | 0.5(200) |
| *Streptococuus mutans* | 5(20) | 5(20) | 1.0(100) | 1.0(100) |
| *Actinomyces viscosus* | 10(10) | 5(20) | 1.0(100) | 1.0(100) |

Experimental Example 2

(Stability)

After keeping the above toothpaste of formulation 1~2 and comparative formulation 1~2 under different temperatures of 0° C., 30° C., 40° C. and 50° C. for 1 week, 1 month and 3 months in a thermostat, the stability of products was identified. The shown in Table 3.

TABLE 3

| Temperature (° C.) | Comp. Formulation 1 | Comp. Formulation 2 | Formulation 1 | Formulation 2 |
|---|---|---|---|---|
| 0 | Stable | Stable | Stable | Stable |
| 30 | Stable | Stable | Stable | Stable |
| 40 | Separated after 1 month | Separated after 2 months | Stable | Stable |
| 50 | Separated after 2 months | Separated after 1 month | Stable | Stable |

EXAMPLE 3

The green tea extracts(50 g) were proportionately loaded inside of precipitated silica(200 g) having particle size of 400 µm by spraying. And then thin slice of carnauba wax(200 g) and loading silica particles were mixed together and heated at a temperature of 85~95° C. The resulting coated green tea extract powder(410 g) were obtained.

EXAMPLE 4

The green tea extracts(50 g) were proportionately loaded inside of Fumed silica(200 g) having a primary particle size of 40 nm by spraying. And then phosphatidylcholine(200 g; having acid value of about 20 and having wax form), one of phospholipids was dissolved into cold ethanol(2,400 g). Prepared phosphatidylcholine-ethanol solution and loading silica particles were mixed together and distilled under reduced pressure with stirring. After ethanol being volatilized, the resulting coated green tea extract powder (410 g) were obtained.

Experimental Example 3
(Stability)

We prepared the toothpaste from oral composition containing above prepared extract powder according to the general toothpaste preparation method with formulation of Table 4 below.

TABLE 4

| INGREDIENT | Comp. Formulation 3 | Formulation 3 | Formulation 4 |
|---|---|---|---|
| Hydrated silicic acid | 17 | 17 | 17 |
| Sodium fluoride | 0.22 | 0.22 | 0.22 |
| Sorbitol solution | 50 | 50 | 50 |
| Carboxy methyl sodium celluose | 1.0 | 1.0 | 1.0 |
| Sodium lauryl sulfate | 2.0 | 2.0 | 2.0 |
| Methyl paraben | 0.15 | 0.15 | 0.15 |
| Flavoring agent | 1.0 | 1.0 | 1.0 |
| Green tea extract | 1.0 | — | — |
| Green tea extract powder(Ex. 3) | — | 1.0 | — |
| Green tea extract powder(Ex. 4) | — | — | 1.0 |
| Titanium dioxide | 0.4 | 0.4 | 0.4 |
| Sodium saccharin | 0.2 | 0.2 | 0.2 |
| Purified water | To 100 | To 100 | To 100 |

After keeping the above toothpaste of formulation 3~4 and comparative formulation 3 under different temperature of 0° C., 30° C., 40° C. and 50° C. for 1 week, 1 month and 3 months in thermostat, the stability of products was identified. The results are shown in Table 5.

TABLE 5

| Temperature (° C.) | Comp. Formulation 3 | Formulation 3 | Formulation 4 |
|---|---|---|---|
| 0 | Stable | Stable | Stable |
| 30 | Stable | Stable | Stable |
| 40 | Separated after 2 months | Stable | Stable |
| 50 | Separated after 1 month | Stable | Stable |

Experimental Example 4

(Slow-Release Properties)

Spiting mixed solution of saliva out after brushing the teeth with toothpaste of above formulation 3 for 30 seconds, 60 seconds, 90 seconds or 120 seconds and 50 ml beaker. Testing bacilli strains were scratched onto individual agar plates containing the above collected solution in a various concentration. In case of bacillus of periodontal disease after being cultivated at 35° C., for 5 days under anaerobic conditions, their growth were observed. And in case of causative bacillus of tooth decay after being cultivated for 2 days under aerobic conditions, their growth were observed, and the minimum concentration of testing bacillus at which they were not grown were measured to identify the antibacterial action against bacillus of tooth decay and causative bacillus of periodontal disease. The results are shown in Table 6.

(1) Testing Bacillus

① Causative bacillus of Periodontal disease: *Actionbacillus actinomycetecomitans*(ATCC29522), *Fusobacterium nucleatum*(ATCC25586)

② Causative bacillus of tooth decay: *Streptococcus mutans*(NCTC10449), *Actinomyces viscosus*(ATCC15987)

(2) Culture Medium

Blood agar medium(blood agar base+blood which makes the final concentration as 5%), BHI agar

TABLE 6

| Testing bacillus | 30 seconds | 60 seconds | 90 seconds | 120 seconds |
|---|---|---|---|---|
| *Actionbacillus actinomycetemcomitans* | 2(50) | 1(100) | 0.5(200) | 0.5(200) |
| *Fusobacterium nucleatum* | 2(50) | 1(100) | 1(100) | 0.5(200) |
| *Streptococuus mutans* | 5(20) | 5(20) | 2(50) | 1(100) |
| *Actinomyces viscosus* | 10(10) | 5(20) | 1(100) | 1(100) |

The composition of oral composition containing above prepared pine salt of formulation 1~2 and above prepared green tea extract of formulation 3~4 will be described in detail by way of formulation examples 5~18. But, it should not be interpreted that the composition of present invention to be limited to these formulation examples.

Formulation Examples 5~8
(Toothpaste in the Form of Paste)

| Ingredient | Weight % | | | |
|---|---|---|---|---|
| | Formulation 5 | Formulation 6 | Formulation 7 | Formulation 8 |
| Aluminum hydroxide | 47 | — | 47 | — |
| Calcium monohydrogen phosphate | — | 45 | — | 45 |
| Sodium monofluoro phosphate | 0.76 | 0.76 | 0.76 | 0.76 |
| Glycerin | 5 | 10 | 5 | 10 |
| Sorbitol solution | 40 | 40 | 40 | 40 |
| Carboxy methyl sodium celluose | 0.7 | 0.9 | 0.7 | 0.9 |
| Silicon dioxide | 4 | 4 | 4 | 4 |
| Sodium lauryl sulfate | 2 | 2 | 2 | 2 |
| Methyl paraben | 0.15 | 0.15 | 0.15 | 0.15 |
| Flavoring agent | 1.0 | 1.0 | 1.0 | 1.0 |
| PEG 1500 | — | 1.7 | — | 1.7 |
| Pine salt(Ex. 1) | 1.0 | 1.0 | — | — |
| Green tea extract powder(Ex. 3) | — | — | 1 | 1 |
| Titanium dioxide | 0.4 | 0.4 | 0.4 | 0.4 |
| Sodium saccharin | 0.2 | 0.2 | 0.2 | 0.2 |
| Purified water | To 100 | To 100 | To 100 | To 100 |

Formulation Examples 9~16
(Mouthwash)

| INGREDIENT | Formulation 9 | Formulation 10 | Formulation 11 | Formulation 12 | Formulation 13 | Formulation 14 | Formulation 15 | Formulation 16 |
|---|---|---|---|---|---|---|---|---|
| | Weight % | | | | | | | |
| Sodium fluoride | 0.22 | 0.22 | 0.22 | 0.22 | 0.22 | 0.22 | 0.22 | 0.22 |
| Triclosan | 0.03 | 0.02 | — | — | 0.03 | 0.02 | — | — |
| Tranexamic acid | — | — | 0.05 | 0.05 | — | — | 0.05 | 0.05 |
| Glycerin | 3.00 | 3.00 | 3.00 | 3.00 | 3.00 | 3.00 | 3.00 | 3.00 |
| Sorbitol solution | 10.00 | 10.00 | 10.00 | 10.00 | 10.00 | 10.00 | 10.00 | 10.00 |
| Polyethylene glycol | 5.00 | 5.00 | — | — | 5.00 | 5.00 | — | — |
| Poloxamer 407 | — | — | 1.00 | 1.00 | — | — | 1.00 | 1.00 |
| Xylitol | 2.00 | 2.00 | — | — | 2.00 | 2.00 | — | — |
| Ethanol (edible) | 5.00 | 5.00 | 5.00 | 5.00 | 5.00 | 5.00 | 5.00 | 5.00 |
| Sodium saccharin | 0.10 | 0.10 | 0.10 | 0.10 | 0.10 | 0.10 | 0.10 | 0.10 |
| Polyoxyethylene hardened castor oil | 2.50 | 2.50 | 2.50 | 2.50 | 2.50 | 2.50 | 2.50 | 2.50 |
| Sodium lauryl sulfate | 0.20 | 0.20 | 0.20 | 0.20 | 0.20 | 0.20 | 0.20 | 0.20 |
| Pine salt (Ex. 2) | 0.10 | 0.10 | 0.10 | 0.10 | — | — | — | — |
| Green tea extract powder (Ex. 4) | — | — | — | — | 0.10 | 0.10 | 0.10 | 0.10 |
| Flavoring agent | 0.20 | 0.20 | 0.20 | 0.20 | 0.20 | 0.20 | 0.20 | 0.20 |
| l-methol | 0.20 | 0.20 | 0.20 | 0.20 | 0.20 | 0.20 | 0.20 | 0.20 |
| Purified water | To 100 | To 100 | To 100 | To 100 | To 100 | To 100 | To 100 | To 100 |

Formulation Example 17~
(Oral Refrigerant)

| Ingredient | Weight % | |
|---|---|---|
| | Formulation 17 | Formulation 18 |
| Sodium fluoride | 0.05 | 0.05 |
| Ethanol(edible) | 0.05 | 0.05 |
| Sorbitol solution | 30.0 | 30.0 |
| Flavoring agent | 5.00 | 5.00 |
| Sodium saccharine | 0.50 | 0.50 |
| Pine salt(Ex. 2) | 0.10 | — |
| Green Tea Extract powder(Ex. 4) | — | 0.10 |
| Purified water | To 100 | To 100 |

What is claimed is:

1. A method for preparation of a coated plant extract powder which comprises the steps of (a) loading one or more plant extracts having activities of prevention of and treatment for periodontal diseases or tooth decay into a porous powder carrier; and (b) coating said carrier's surface with a water-insoluble coating agent,
   wherein said water-insoluble coating agent is selected from the group consisting of methyl cellulose, hydroxypropylcellulose, hydroxypropylmethylcellulose, ethylcellulose, hydroxyethylcellulose, polyvinylalcohol, vinylpyrrolidone, vinylacetate copolymer, polyvinylacetaldimethylaminoacetate, polymethylmethacrylate, beeswax, paraffin wax, carnauba wax, petroleum wax, polyhydroxyalkanoic acids, glycolipids, glycerides and phospholipids.

2. A method for preparation of a coated plant extract powder according to claim 1, in which a ratio of carrier and coating agent is 1:0.5~10 by weight.

3. A method for preparation of a coated plant extract powder according to claim 1, in which said plant extract is selected from the group consisting of pine, licorice, cassia seed, cinnamon, nothosmyrnium root, sophora, lonicera flower, platycodon, green tea, dayflower, Korean angelica root, liriope rhizome, moutan, Arabian myrrh, seseleos radix, *Angelicae Dahuricae Radix, Lagerstroemia indica*, morus bark, ginger, sanguinaria, asarum, cimicifuga, Chinese galls, Grapefruit seed, lycium root, cnidium, *Alpinia katsumadai Hayata*, gardenia, *Lythrum salicaria L.*, dandelion, propolis, flavonoid, nepta herb, *Reynoutria japonica Houtt.*, scutellaria, machilia, black adzuki bean, camomile, ratanhia and Sage oil.

4. A method for preparation of a coated plant extract powder according to claim 3, wherein said plant extract is pine extract, and is mixed with salt at a ratio of 1:0.1–10 by weight.

5. A method for preparation of a coated plant extract powder according to claim 1, wherein said carrier is porous materials having a particle size of 100–600 μm or fumed silica having a primary particle size of 1–100 nm.

6. A method for preparation of a coated plant extract powder according to claim 5, wherein said porous material is selected from group consisting of calcium monohydrogen phosphate, calcium pyrophosphate, calcium carbonate, silicon dioxide, aluminum hydroxide, insoluble sodium metaphosphate, aluminum silicate, zirconium silicate, aluminum magnesium silicate, diatomite, zirconium oxide, polyethylenes, polyvinylchlorides, polyesters, polystyrenes, polypropylenes, polyamides, polycarbonates, phenol resins, urea resins, polymethylmetacrylate resins and melamine resins.

* * * * *